United States Patent
Kitanoya et al.

(10) Patent No.: US 6,325,906 B1
(45) Date of Patent: Dec. 4, 2001

(54) GAS SENSOR AND APPARATUS FOR MEASURING COMBUSTIBLE GAS COMPONENT CONCENTRATION USING THE SAME

(75) Inventors: Shoji Kitanoya; Tomohiro Fuma; Kenji Kato, all of Aichi; Ryuji Inoue, Gife; Takafumi Oshima, Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/453,540

(22) Filed: Dec. 3, 1999

(30) Foreign Application Priority Data

Dec. 4, 1998 (JP) .................................. 10-345024

(51) Int. Cl.$^7$ ...................... G01N 27/407; G01N 27/409; G01N 27/41
(52) U.S. Cl. .......................... 204/425; 204/426; 204/427; 205/787
(58) Field of Search .................................. 204/424–429; 73/23.32; 205/784.5, 785, 787

(56) References Cited

U.S. PATENT DOCUMENTS

| | | | |
|---|---|---|---|
| 4,722,779 | * | 2/1988 | Yamada et al. ........................ 204/410 |
| 4,765,880 | * | 8/1988 | Hayakawa et al. .................... 204/425 |
| 5,250,169 | | 10/1993 | Logothetis et al. . |
| 5,281,313 | | 1/1994 | Visser et al. . |
| 5,433,830 | * | 7/1995 | Kawai et al. .......................... 204/425 |
| 5,630,920 | * | 5/1997 | Friese et al. .......................... 204/424 |
| 5,879,525 | | 3/1999 | Kato ...................................... 204/424 |
| 5,893,968 | | 4/1999 | Kato ................................... 205/784.5 |
| 5,895,564 | * | 4/1999 | Miyata et al. ....................... 205/784.5 |
| 5,985,118 | * | 11/1999 | Makino et al. ........................ 204/426 |

FOREIGN PATENT DOCUMENTS 0 902 279 A1  3/1999  (EP) .
0 903 576 A2  3/1999  (EP) .

* cited by examiner

Primary Examiner—Robert J. Warden, Sr.
Assistant Examiner—Kaj K. Olsen
(74) Attorney, Agent, or Firm—Sughrue, Mion, Zinn, Macpeak & Seas, PLLC

(57) ABSTRACT

A gas sensor includes a first processing chamber 3 into which a gas under measurement is introduced through a first gas passage 2; a second processing chamber 5 into which the gas is introduced from the first processing chamber 3 through a second gas passage 4 and in which combustible gas components burn; a third gas passage 15 for introducing $O_2$ into the second processing chamber 5 under diffusion resistance; oxygen pump element 12 adapted to pump out $O_2$ from or pump into the first processing chamber 3 on the basis of an output from an oxygen-concentration sensor 13, which senses the oxygen concentration of the gas introduced into the second processing chamber 5, to thereby control the oxygen concentration of the gas; and a second oxygen pump including a second inner electrode 10 and a second outer electrode 11 formed on an oxygen-ion conductor 1 in such a manner as to face the interior and exterior, respectively, of the second processing chamber 5, and adapted to pump out $O_2$ which remains unconsumed in burning mentioned above in the second processing chamber 5, through application of a constant voltage between the second inner electrode 10 and the second outer electrode 11. The residual oxygen concentration of the second processing chamber 5 is determined on the basis of a second oxygen pump current flowing between the second inner and outer electrodes 10 and 11, whereby the concentration of combustible gas components contained in the gas under measurement is determined.

8 Claims, 3 Drawing Sheets

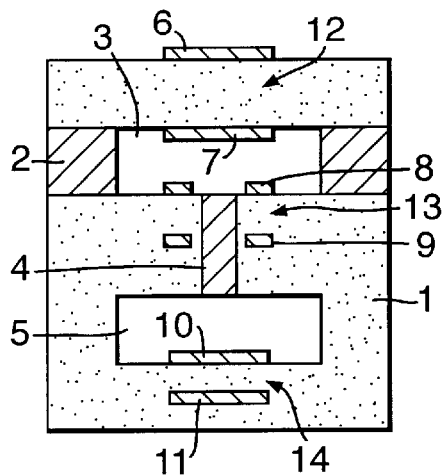
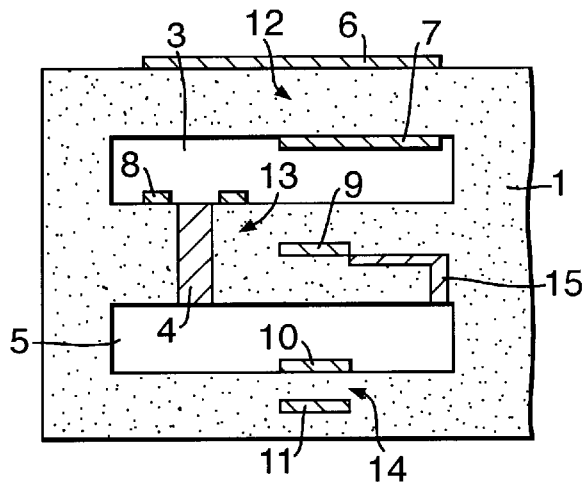
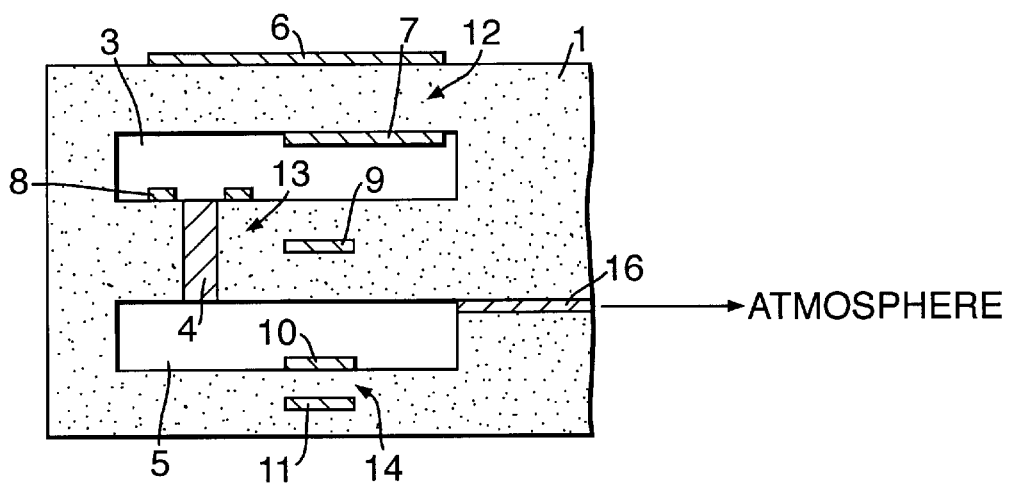

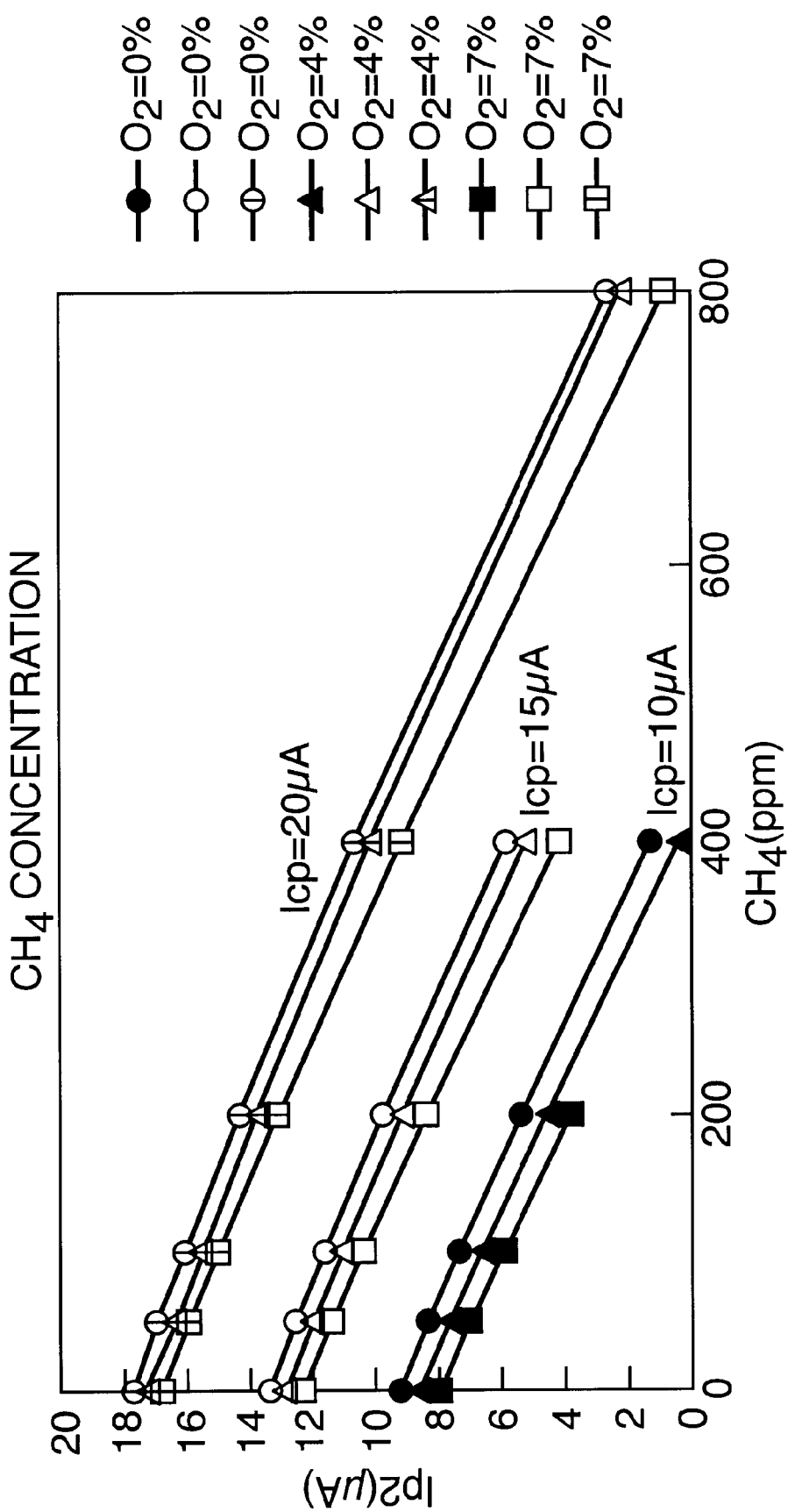

GAS SENSOR AND APPARATUS FOR MEASURING COMBUSTIBLE GAS COMPONENT CONCENTRATION USING THE SAME

BACKGROUND OF THE INVENTION

The present invention relates to a gas sensor for measuring the concentration of a combustible gas component. More particularly, the invention relates to a gas sensor for measuring the concentration of a combustible gas component contained in exhaust gas from an internal combustion engine, and to an apparatus for measuring combustible gas component concentration by use of the gas sensor.

Japanese Patent Application Laid-Open (kokai) No. 8-247995 discloses an apparatus for measuring combustible gas component concentration having the following structure. In this apparatus, a gas under measurement which contains combustible gas components is introduced into a first processing zone. By means of a first oxygen pump cell, the partial pressure of oxygen is reduced to a predetermined low value ($10^{-14}$ atm or less) at which combustible gas components remain substantially unburned. The thus-controlled atmosphere is introduced into a second processing zone. The combustible gas components contained in the atmosphere are burned with $O_2$ which is pumped into the second processing zone by means of a second oxygen pump cell. At this time, pump current flowing through the second oxygen pump cell or voltage developed between electrodes of the second oxygen pump cell is detected. The combustible gas component concentration of the gas under measurement is determined from the detected value.

In the above-described apparatus for measuring combustible gas component concentration proposed in Japanese Patent Application Laid-Open (kokai) No. 8-247995, when $O_2$ remains in the second processing zone, combustible gas components first burn through reaction with the residual $O_2$. Accordingly, upon variation in the amount of $O_2$ remaining in the second processing zone, no proportional relationship is established between the amount of $O_2$ which is pumped into the second processing zone by means of the second oxygen pump cell and the amount of combustible gas components contained in the second processing zone. That is, this measuring apparatus suffers a measurement error, since, upon variation in the amount of $O_2$ remaining in the second processing zone, no proportional relationship is established between current flowing through the second oxygen pump cell and the combustible gas component concentration of the second processing zone.

To avoid the above-mentioned problem, the partial pressure of oxygen contained in gas introduced into the second processing zone from the first processing zone must be reduced to a significantly low, constant level ($10^{-14}$ atm or less). To fulfill this requirement, a driving force applied to the first oxygen pump cell must be increased, raising a new problem in that a burden imposed on the first oxygen pump cell increases. Additionally, if the partial pressure of oxygen is reduced excessively, dissociation of water will occur in the second processing zone, raising another problem in that a measurement error occurs.

Further, in this measuring apparatus, the operation of the second oxygen pump cell must be controlled such that the partial pressure of oxygen in the second processing zone becomes constant. To fulfill this requirement, in addition to the second oxygen pump cell, another element (e.g., oxygen concentration cell element) for measuring the partial pressure of oxygen in the second processing zone must be provided. Accordingly, the number of elements provided on the second processing zone side increases, causing complication of the sensor structure with a resultant increase in fabrication cost. Also, since the second oxygen pump cell is operated after detection of the partial pressure of oxygen in the second processing zone, responsiveness becomes poor.

SUMMARY OF THE INVENTION

An object of the present invention is to provide a gas sensor having a simple structure and capable of measuring combustible gas components at high accuracy and over a wide range, as well as to provide a measuring apparatus using the gas sensor.

A gas sensor of the present invention includes the following means:

(1) Oxygen pump means (combustible-gas-component sensing element) for pumping out from a second processing chamber to the exterior thereof $O_2$ remaining in the second processing chamber; i.e., $O_2$ remaining unconsumed in burning of combustible gas components; and (2) A third gas passage for stably introducing a predetermined amount of $O_2$ into the second processing chamber under diffusion resistance.

The gas sensor of the present invention also includes means for stabilizing the oxygen concentration of the second processing chamber to a possible extent through diffusion of $O_2$ into the second processing chamber in addition to introduction of $O_2$ into the second processing chamber through a second gas passage.

In the case where the gas sensor of the present invention is not provided with the third gas passage, the gas sensor can only measure combustible gas concentration over a range (a low-concentration range) corresponding to the amount of $O_2$ remaining in a first processing chamber. Through employment of the third gas passage, $O_2$ is introduced into the second processing chamber through the third gas passage in a predetermined amount required for substantially completely burning combustible gas components, thereby expanding a measurable concentration range.

Additionally, the gas sensor of the present invention eliminates the need to control to a significantly low, constant level the oxygen concentration of gas diffused from the first processing chamber to the second processing chamber. Also, it is not mandatory to detect the oxygen concentration of the second processing chamber and control the oxygen concentration of the second processing chamber to a significantly low, constant level according to the detected oxygen concentration. Thus, there is no need for providing respective oxygen-concentration sensing means which face the interiors of the first and second processing chambers. Particularly, it is not mandatory to detect the oxygen concentration of the second processing chamber. Accordingly, the present invention simplifies a gas sensor structure.

The operation of the gas sensor of the present invention will next be described. A gas under measurement which contains $O_2$ and combustible gas components diffuses from an atmosphere to be measured to the first processing chamber. $O_2$ is pumped out from or pumped into the first processing chamber to thereby control to a low level the oxygen concentration of the gas diffusing into the second processing chamber. As a result of this pumping-out or pumping-in operation, a first oxygen pump current flows through the oxygen-ion conductor of first oxygen pump means according to the oxygen concentration of the gas under measurement. The gas having oxygen concentration controlled to a low level diffuses into the second processing chamber. Additionally, sufficient $O_2$ is introduced into the second processing chamber through the third gas passage under diffusion resistance. A portion of $O_2$ introduced into the second processing chamber is consumed through reaction with combustible gas components; i.e., through burning of combustible gas components. $O_2$ which remains unconsumed in burning of combustible gas components is pumped out from the second processing chamber under a constant driving force provided by the second oxygen pump means. As a result of this pumping-out operation, a second oxygen pump current flows through the oxygen-ion conductor of the second oxygen pump means according to the amount of residual $O_2$ pumped-out from the second processing chamber. Through introduction of $O_2$ into the second processing chamber through the third gas passage, the oxygen concentration of the second processing chamber is stably maintained at a relatively high level. Thus, in principle, the second oxygen pump current is inversely proportional to the combustible gas component concentration of the second processing chamber. Therefore, information regarding the concentration of combustible gas components contained in the gas under measurement can be obtained on the basis of the value of the second oxygen pump current.

BRIEF DESCRIPTION OF THE DRAWINGS

Embodiments of the invention will now be described, by way of example only, with reference to the accompanying drawings, in which:

FIGS. 1(A) and (B) give views for explaining a gas sensor according to an embodiment of the present invention, wherein (A) is a lateral sectional view and (B) is a longitudinal sectional view of an end portion;

FIG. 3 is a graph for explaining the results of measuring $CH_4$ gas concentration by use of the measuring apparatus of FIG. 2; and FIG. 4 is a longitudinal sectional view for explaining a gas sensor according to another embodiment of the present invention, showing an end portion of the sensor.

Figure 2:
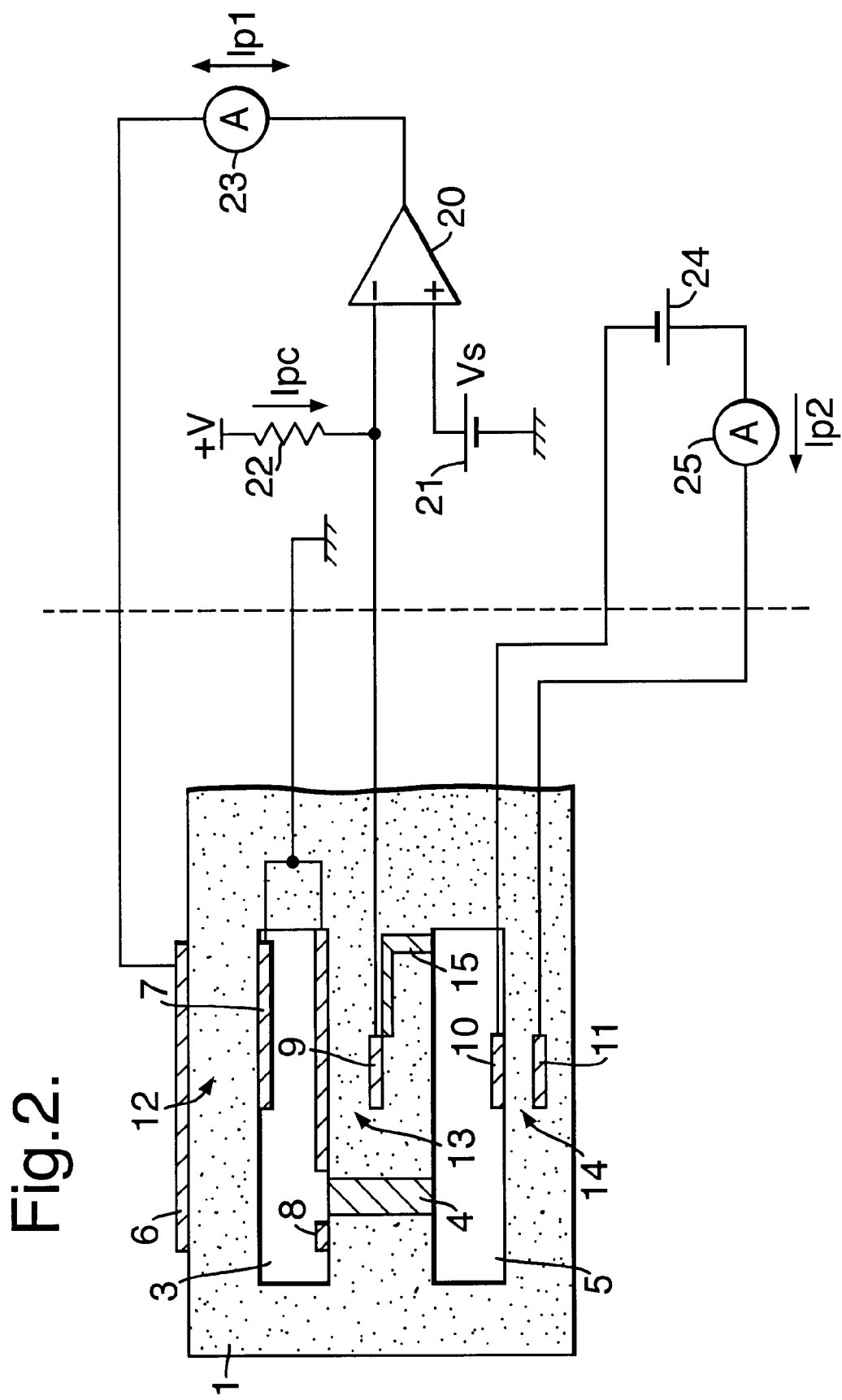
FIG. 2 is a view for explaining a measuring apparatus which uses the gas sensor of FIG. 1(A) and FIG. 1(B)

In the drawings, reference numerals are used to identify items as follows:
1: structure formed with oxygen-ion conductor
2: first gas passage
3: first processing chamber
4: second gas passage
5: second processing chamber
6: first outer electrode
7: first inner electrode
8: oxygen-concentration sensing electrode
9: oxygen-concentration reference electrode
10: second inner electrode
11: second outer electrode
12: oxygen pump element (first oxygen pump means)
13: oxygen-concentration sensing element (oxygen-concentration sensing means)
14: combustible-gas-concentration sensing element (second oxygen pump means)
15, 16: third gas passage
Ip1: first oxygen pump current
Ip2: second oxygen pump current
Icp: reference-electrode self-induced current

DETAILED DESCRIPTION

A preferred mode for carrying out the invention will first be described.

According to the preferred mode for carrying out the invention, a gas sensor is mainly composed of a plurality of layers of oxygen-ion conductor (solid electrolyte), and includes a first processing chamber and a second processing chamber, each being isolated from their surroundings by the oxygen-ion conductor. A solid solution of $ZrO_2$ containing $Y_2O_3$ or CaO is a typical material for the oxygen-ion conductive solid electrolyte layer. Alternatively, the solid electrolyte layer may be formed of a solid solution of $ZrO_2$ and an oxide of an alkaline earth metal or rare-earth metal. $ZrO_2$, which is a base component of the solid electrolyte layer, may contain $HfO_2$. Further, partially stabilized and/or stabilized $ZrO_2$, $CeO_2$, $HfO_2$, and $ThO_2$ may be used. One or more stabilizers may be selected from among, for example, CaO, MgO, and rare-earth oxides (e.g., $Y_2O_3$, $La_2O_3$, and $Gd_2O_3$). Preferably, a sintered body of yttrium partially stabilized zirconia (YSZ) is used as a stabilizer. Other stabilizers or other solid electrolytes may also be used.

According to the preferred mode for carrying out the invention, the gas sensor is fabricated by a known method in which green sheets are laminated and fired. For example, there are laminated plain $ZrO_2$ green sheets and $ZrO_2$ green sheets which are coated with a predetermined paste or in which a porous ceramic element is embedded, in order to form a porous electrode, gas passage, or processing chamber. The resultant laminate is dried and fired, yielding a gas sensor.

In the gas sensor according to the preferred mode for carrying out the invention, first to third gas passages assume the form of a porous element of, for example, ceramic, fine through-holes, or fine slits. Preferably, the gas passages assume the form of a porous alumina element.

In the gas sensor according to the preferred mode for carrying out the invention, an oxygen-concentration reference electrode and an oxygen-concentration sensing electrode are formed on or in the same oxygen-ion conductor, while the oxygen-concentration reference electrode is electrically connected to the positive pole side of a power supply, thereby implementing means for conducting a small oxygen pump current between the oxygen-concentration reference electrode and the oxygen-concentration sensing electrode. Thus, oxygen ions generated through dissociation of $O_2$ on the oxygen-concentration sensing electrode move to the oxygen-concentration reference electrode through the oxygen-ion conductor, whereby a small oxygen pump current; i.e., a reference-electrode self-induced current Icp, flows. The self-reference-electrode-induced current Icp is preferably 5–50 $\mu$A, more preferably about 15 $\mu$A.

In the gas sensor according to the preferred mode for carrying out the invention, a first inner electrode assumes a multilayer structure including a first electrode portion and a second electrode portion. The first electrode portion contains Pt as a main component. The second electrode portion is formed on the first electrode portion or is formed in such a manner as to cover the first electrode portion. The second electrode portion contains a main component selected singly or in combination from the group consisting of Au, Ag, Cu, Pt—Au alloys, Au—Pd alloys, Pt—Ag alloys, and Pt—Ni alloys. The first electrode portion has high catalytic capability to decompose $O_2$ into oxygen ions and capability to pump oxygen ions. As compared with the first electrode portion, the second electrode portion exhibits low catalytic capability to accelerate the reaction of combustible gas components and $O_2$. Through employment of the multilayer structure, burning of a combustible gas is suppressed in the first processing chamber.

In the gas sensor according to the preferred mode for carrying out the invention, the third gas passage is formed such that the second processing chamber communicates with an atmosphere (oxygen source) in which oxygen concentration is stabilized at a high level. Examples of the oxygen source include the interior or vicinity of the oxygen-concentration reference electrode serving as a self-reference electrode, the interior or vicinity of an electrode from which $O_2$ is pumped out, a space from which $O_2$ is pumped out, and the atmosphere. The amount of $O_2$ introduced into the second processing chamber through the third gas passage is adjusted such that the reference-electrode self-induced current Icp flows in an amount of 5–50 $\mu$A, preferably about 15 $\mu$A. In the gas sensor according to the preferred mode for carrying out the invention, the oxygen concentration of the second processing chamber is controlled to $10^{-6}$–$10^{-12}$ atm, preferably $10^{-7}$–$10^{-9}$ atm. A constant voltage of, for example, 300–600 mV is applied between the second inner electrode and the second outer electrode. The constant voltage to be applied depends on the specific conditions.

In the gas sensor according to the preferred mode for carrying out the invention, an oxidation catalyst section is provided in such a manner as to face the interior of the second processing chamber in order to accelerate the reaction of $O_2$ and combustible gas components, such as HC gas and CO gas; i.e., burning of combustible gas components. Through employment of a Pt electrode as the second inner electrode, the second inner electrodes serves as the oxygen catalyst section. Preferably, the electrodes of the gas sensor assume the form of a porous electrode in order to improve a predetermined catalytic capability or oxygen-pumping capability.

In order to clarify the above-described mode for carrying out the invention, a more detailed embodiment of the present invention will next be described with reference to the accompanying drawings.

FIG. 1(A) and FIG. 1(B) are views for explaining the structure of a gas sensor according to embodiment 1 of the present invention, wherein FIG. 1(A) is a lateral sectional view and FIG. 1(B) is a longitudinal sectional view of an end portion.

Referring to FIG. 1(A) and FIG. 1(B), a gas sensor includes a structure 1 composed of a plurality of layers of oxygen-ion conductor. The structure 1 has a first processing chamber 3 and a second processing chamber 5 formed therein in a manner isolated from their surroundings. The first processing chamber 3 communicates with the exterior of the structure 1 (atmosphere under measurement) through a first gas passage 2 having diffusion resistance. The first and second processing chambers 3 and 5 communicate with each other through a second gas passage 4. An opening of the first gas passage 2 that faces the first processing chamber 3, and an opening of the second gas passage 4 that faces the first processing chamber 3 are located sufficiently apart from each other with respect to a gas flow direction.

A first outer electrode 6 and a first inner electrode 7 are formed on an oxygen-ion conductor layer that isolates the first processing chamber 3 from its exterior, in such a manner as to face the exterior and interior, respectively, of the first processing chamber 3. The length of the first outer electrode 6 is longer than that of the first inner electrode 7 along a basic flow direction of gas flowing from the first gas passage 2 to the second gas passage 4. This oxygen-ion conductor layer, the first outer electrode 6, and the first inner electrode 7 constitute an oxygen pump element (first oxygen pump means) 12.

An oxygen-concentration sensing electrode 8—which faces the interior of the first processing chamber 3—and an oxygen-concentration reference electrode 9—which does not face the first processing chamber 3—are formed on another oxygen-ion conductor layer. The oxygen-concentration sensing electrode 8 is formed around an opening of the second gas passage 4 that faces the first processing chamber 3. The oxygen-concentration reference electrode 9 is embedded in the oxygen ion conductor layer. This oxygen ion conductor layer, the oxygen-concentration sensing electrode 8, and the oxygen-concentration reference electrode 9 constitute an oxygen-concentration sensing element (oxygen-concentration sensing means) 13.

A second inner electrode 10—which faces the interior of the second processing chamber 5—and a second outer electrode 11—which faces toward the exterior of the second processing chamber 5—are formed on still another oxygen-ion conductor layer. The second outer electrode 11 is embedded in the oxygen-ion conductor layer. This oxygen-ion conductor layer, the second inner electrode 10, and the second outer electrode 11 constitute a combustible-gas-concentration sensing element (second oxygen pump means) 14.

Referring to FIG. 1(B), a third gas passage 15 is formed in the structure 1 formed with oxygen-ion conductor, in such a manner as to establish communication between the oxygen-concentration reference electrode 9 and the second processing chamber 5. The third gas passage 15 is preferably formed with a porous material of alumina and adapted to diffuse $O_2$ toward the oxygen-concentration reference electrode 9 or the second processing chamber 5, whichever has lower oxygen concentration (partial pressure).

Next will be described an apparatus for measuring combustible gas components by use of the gas sensor shown in FIG. 1, and the operation of the measuring apparatus. FIG. 2 is a view for explaining the measuring apparatus. Referring to FIG. 2, in the measuring apparatus, the first inner electrode 7 and the oxygen-concentration sensing electrode 8 are grounded. Reference voltage Vs is input from a reference voltage source 21 to a noninverted input terminal (+) of a differential amplifier 20. The oxygen-concentration reference electrode 9 is connected to an inverted input terminal (−) via a lead portion. As a result, an electric potential difference between the oxygen-concentration sensing electrode 8 and the oxygen-concentration reference electrode 9 (electromotive force induced by oxygen concentration cell effect) is input to the inverted input terminal. One end of a resistor 22 is electrically connected to a node located between the inverted input terminal (−) and the oxygen-concentration reference electrode 9. The other end of the resistor 22 is connected to a positive side of a power supply. Thus, a reference-electrode self-induced current Icp flows between the oxygen-concentration reference electrode 9 and the oxygen-concentration sensing electrode 8, whereby oxygen ions generated through dissociation on the oxygen-concentration sensing electrode 8 are conducted toward the oxygen-concentration reference electrode 9 through the oxygen-ion conductor layer. $O_2$ pumped out through this conduction of oxygen ions establishes a stable reference-oxygen-concentration atmosphere of a predetermined level within or in the vicinity of the oxygen-concentration reference electrode 9.

The output terminal of the differential amplifier 20 is electrically connected to the first outer electrode 6 through a lead portion. The differential amplifier 20 variably applies voltage between the first outer electrode 6 and the first inner electrode 7 such that the electrical potential difference between the oxygen-concentration sensing electrode 8 and the oxygen-concentration reference electrode 9 becomes equal to reference voltage Vs. Oxygen ions generated through dissociation of $O_2$ on the first outer electrode 6 or the first inner electrode 7 are conducted through the oxygen-ion conductor layer to become $O_2$ again on the other electrode. Thus, a first pump current Ip1 flows in a regular or reverse direction through a first ammeter 23 connected between the output terminal of the differential amplifier 20 and the first outer electrode 6, according to the oxygen concentration of the first processing chamber 3; i.e., the oxygen concentration of an atmosphere under measurement. On the basis of this first pump current Ip1, the oxygen concentration of a gas under measurement can be determined.

The negative-pole side of a constant-voltage power supply 24 is electrically connected to the second inner electrode 10, and its positive-pole side is electrically connected to the second outer electrode 11. Thus, a constant voltage is applied between the second inner electrode 10 and the second outer electrode 11, whereby $O_2$ is consumed through oxidation (burning) of combustible gas components on the second inner electrode 10, and oxygen ions generated through dissociation of residual $O_2$ are conducted through the oxygen-ion conductor layer to become $O_2$ again on the second outer electrode 11. An ammeter 25 is connected between the positive side of the constant-voltage power supply 24 and the second outer electrode 11. A second pump current Ip2 flows through the ammeter 25 according to combustible gas concentration.

The function of the third gas passage 15 will next be described with reference to FIG. 2. As described above, the oxygen-concentration reference electrode 9 is a self-generation-type reference electrode and has a stable reference-oxygen-concentration atmosphere of a predetermined level therein or in the vicinity thereof. $O_2$ is introduced from this reference-oxygen-concentration atmosphere to the second processing chamber 5 through the third gas passage 15 under a predetermined diffusion resistance, thereby raising the oxygen concentration of the second processing chamber 5 (stabilizing the oxygen concentration at a relatively high level).

Next will be described the combustible-gas-concentration measuring principle of the measuring apparatus of FIG. 2. A gas under measurement that contains combustible gas components and $O_2$ diffuses into the first processing chamber 3 through the first gas passage 2. The oxygen pump element 12 pumps out $O_2$ from the first processing chamber 3 according to a detection output from the oxygen-concentration sensing element 13 and such that the oxygen concentration of a gas introduced into the second processing chamber 5 becomes constant ($O_2$ may be pumped into the first processing chamber 3 depending on concentration corresponding to reference voltage Vs). The first oxygen pump current Ip1 that flows at this time is basically proportional to the oxygen concentration of the gas under measurement. The gas having a controlled oxygen concentration diffuses into the second processing chamber 5 through the second gas passage 4. Combustible gas components burn ($O_2$ is consumed) through reaction with $O_2$ on the second inner electrode 10, which contains a catalytic component. The combustible-gas-concentration sensing element 14 causes unconsumed residual $O_2$ to be decomposed into oxygen ions on the second inner electrode 10 and causes the generated oxygen ions to be pumped out to the exterior of the gas sensor. As a result, the second oxygen pump current Ip2 flows. Since the amount of residual $O_2$ varies in inverse proportion to the amount of combustible gas components, this second oxygen pump current Ip2 is basically in inverse proportion to the combustible gas concentration of the second processing chamber 5. Accordingly, on the basis of the second oxygen pump current Ip2, the combustible gas concentration of the gas under measurement can be measured.

Next, measurement of the concentration of $CH_4$, which is a combustible gas component, by use of the above-described apparatus for measuring combustible gas component concentration (see FIG. 2) will be described by way of example. In the measuring apparatus of FIG. 2 used in this example, a porous electrode of Pt was used as the first outer electrode 6; a porous two-layer electrode of Pt—Au (Pt: inside; Au: outside) was used as the first inner electrode 7; a porous electrode of Pt-1 wt % Au was used as the oxygen-concentration sensing electrode 8; a porous electrode of Pt was used as the oxygen-concentration reference electrode 9; a porous electrode of Pt-1 wt % Au was used as the second inner electrode 10; a porous electrode of Pt was used as the second outer electrode 11; and porous alumina was used as material for the first through third gas passages 2, 4, and 15. Reference voltage Vs assumed a value of 450 mV (corresponding to an oxygen concentration of $10^{-9}$ atm); a voltage of about 450 mV was applied between the first inner electrode 6 and the first outer electrode 7; a constant voltage of 350 mV was applied between the second inner electrode 10 and the second outer electrode 11; and the oxygen concentration of the second processing chamber 5 was set to about $10^{-7}$ atm.

A reference-electrode self-induced current Icp was set to 10 $\mu$A, 15 $\mu$A, and 20 $\mu$A. The basic composition of a gas under measurement was 10% $H_2O$, 10% $CO_2$, 0%, 4%, and 7% $O_2$, and $N_2$ as balance and contained $CH_4$ as a combustible gas component in an amount of 0–800 ppm. The gas under measurement having a temperature of 300° C. was fed to the gas sensor of FIG. 2 at a total flow rate of 15 L/min, and the second oxygen pump current Ip2 was measured.

FIG. 3 is a graph for explaining the results of measuring $CH_4$ gas concentration by use of the measuring apparatus of FIG. 2. As seen from FIG. 3, this measuring apparatus provides a linear sensor output (second oxygen pump current Ip2) with $CH_4$ gas concentration and is less susceptible to oxygen concentration. Variation in output (variation in an offset value of the second oxygen pump current Ip2) as observed at a $CH_4$ concentration of 0 ppm and each oxygen concentration, and variation in sensitivity (variation in inclination of the second oxygen pump current Ip2) can be corrected on the basis of the oxygen concentration of the first processing chamber; i.e., the first oxygen pump current Ip1 or an output from the oxygen-concentration sensing element 13.

Also, it was confirmed that, as the reference-electrode self-induced current Icp is increased in the order of 10 $\mu$A, 15 $\mu$A, and 20 $\mu$A, sensor output (second oxygen pump current Ip2) as a whole rises accordingly. This increase of the reference-electrode self-induced current Icp had substantially no effect on the inclination, linearity, and oxygen concentration dependency of $CH_4$ sensitivity (straight line). Therefore, through increase of the reference-electrode self-induced current Icp, the range of measurement of $CH_4$ gas concentration can be expanded.

FIG. 4 is a longitudinal sectional view for explaining a gas sensor according to another embodiment of the present invention, showing an end portion of the sensor. In order to avoid redundancy, the above description of the gas sensor and FIGS. 1(A) and 1(B) are to be referred to for structural features of the gas sensor of FIG. 4 similar to those of the gas sensor of FIGS. 1(A) and 1(B). Different structural features between the above-described embodiment and the present embodiment will mainly be described. Similar structural or functional features are denoted by common reference numerals in FIG. 4 and FIGS. 1(A) and 1(B).

Referring to FIG. 4, in the gas sensor according to the present embodiment, a third gas passage 16 is formed in an oxygen-ion conductor layer such that the interior of the second processing chamber 5 and the atmosphere communicate with each other under diffusion resistance. The amount of $O_2$ to be introduced into the second processing chamber 5 through the third gas passage 16 can be controlled by adjusting the diffusion resistance (diffusion-controlling condition) of the third gas passage.

The present invention provides a gas sensor having a simple structure and capable of measuring combustible gas component concentration at high accuracy and over a wide range, as well as providing a measuring apparatus using the gas sensor.

What is claimed is:

1. A gas sensor comprising:
    a first processing chamber and a first gas passage for introducing a gas under measurement into said first processing chamber;
    a second processing chamber and a second gas passage for introducing the gas from said first processing chamber into said second processing chamber, said second processing chamber being provided for the reaction therein of combustible gas components contained in the gas with
    a third gas passage for introducing a gas containing $O_2$ into said second processing chamber under diffusion resistance in a predetermined amount in excess of that needed to react with combustible gas components present in the second processing chamber;
    an oxygen-concentration sensor for sensing the oxygen concentration of the gas introduced from said first processing chamber to said second processing chamber;
    a first oxygen pump comprising a first inner electrode and a first outer electrode formed on an oxygen-ion conductor in such a manner as to face the interior and exterior, respectively, of said first processing chamber, said first oxygen pump decomposing $O_2$ into oxygen ions through application of voltage between the first inner electrode and the first outer electrode on the basis of an oxygen-concentration output from said oxygen-concentration sensor and pumping out the generated oxygen ions from or pumping into said first processing chamber through the oxygen-ion conductor to thereby control the oxygen concentration of the gas introduced from said first processing chamber to said second processing chamber;
    means for accelerating the reaction of $O_2$ and combustible gas components contained in the gas introduced into said second processing chamber; and
    a second oxygen pump comprising a second inner electrode and a second outer electrode formed on an oxygen-ion conductor in such a manner as to face the interior and exterior, respectively, of said second processing chamber, said second oxygen pump decomposing into oxygen ions $O_2$ which remains unconsumed in reaction with combustible gas components in said second processing chamber, through application of a constant voltage between the second inner electrode and the second outer electrode and pumping out the generated oxygen ions from said second processing chamber through the oxygen-ion conductor.

2. A gas sensor according to claim 1, wherein said third gas passage is in communication with said second processing chamber and an oxygen source having a partial pressure of oxygen higher than that of said second processing chamber.

3. A gas sensor according to claim 2, wherein:
    said oxygen-concentration sensor comprises an oxygen-concentration sensing electrode formed on the oxygen-ion conductor in such a manner as to be in contact with the gas introduced from said first processing chamber to said second processing chamber, and an oxygen-concentration reference electrode formed on the oxygen-ion conductor and generating a reference electrical-potential for the oxygen-concentration sensing electrode;
    said gas sensor further comprises means for conducting an oxygen pump current between the oxygen-concentration reference electrode and the oxygen-concentration sensing electrode such that an atmosphere having an oxygen concentration higher than at least that of said second processing chamber is established within or in the vicinity of the oxygen-concentration reference electrode;
    said third gas passage is provided in contact with the oxygen-concentration reference electrode; and
    $O_2$ is introduced from the atmosphere having an oxygen concentration higher than at least that of said second processing chamber and established within or in the vicinity of the oxygen-concentration reference electrode to said second processing chamber, through said third gas passage under a predetermined diffusion resistance.

4. A gas sensor according to claim 1, wherein the first inner electrode comprises a multilayer structure including a first electrode portion having a catalytic capability to decompose $O_2$ into oxygen ions and a second electrode portion formed on the first electrode portion and having a catalytic capability to accelerate the reaction of combustible gas components and $O_2$.

5. An apparatus for measuring combustible gas component concentration, comprising a gas sensor according to claim 1 adapted to determine the concentration of combustible gas components contained in the gas under measurement while correcting the combustible gas component concentration for the oxygen concentration of the gas under measurement on the basis of a first oxygen pump current flowing between the first inner electrode and the first outer electrode and a second oxygen pump current flowing between the second inner electrode and the second outer electrode.

6. A gas sensor comprising:
    a first processing chamber and a first gas passage for introducing a gas under measurement into said first processing chamber;
    a second processing chamber and a second gas passage for introducing the gas from said first processing chamber into said second processing chamber, said second processing chamber burning combustible gas components contained in the gas with oxygen;
    a third gas passage for introducing a gas containing oxygen into said second processing chamber under diffusion resistance in a predetermined amount in excess of that needed to burn combustible gas components in the second processing chamber;
    an oxygen-concentration sensor for sensing the oxygen concentration of the gas introduced from said first processing chamber to said second processing chamber;

a first oxygen pump comprising a first inner electrode and a first outer electrode formed on an oxygen-ion conductor in such a manner as to face the interior and exterior, respectively, of said first processing chamber, and pumping oxygen into or pumping oxygen out of the first processing chamber through application of voltage between the first inner electrode and the first outer electrode on the basis of an oxygen-concentration output from said oxygen-concentration sensor to thereby control the oxygen concentration of the gas introduced from said first processing chamber to said second processing chamber;

means for accelerating the burning of oxygen and combustible gas components contained in the gas introduced into said second processing chamber; and a second oxygen pump comprising a second inner electrode and a second outer electrode formed on an oxygen-ion conductor in such a manner as to face the interior and exterior, respectively, of said second processing chamber, said second oxygen pump pumping out oxygen which remains unconsumed in burning with combustible gas components in said second processing chamber, through application of a constant voltage between the second inner electrode and the second outer electrode.

7. A gas sensor comprising:

a first processing chamber and a first gas passage for introducing a gas under measurement into said first processing chamber;

a second processing chamber and a second gas passage for introducing the gas from said first processing chamber into said second processing chamber, said second processing chamber burning combustible gas components contained in the gas with oxygen;

a third gas passage for introducing a gas containing oxygen into said second processing chamber under diffusion resistance in a predetermined amount in excess of that needed to burn combustible gas components in the second processing chamber;

an oxygen-concentration sensor for sensing the oxygen concentration of the gas introduced from said first processing chamber to said second processing chamber;

a first oxygen pump comprising a first inner electrode and a first outer electrode formed on an oxygen-ion conductor in such a manner as to face the interior and exterior, respectively, of said first processing chamber, and pumping oxygen into or pumping oxygen out of the first processing chamber through application of voltage between the first inner electrode and the first outer electrode on the basis of an oxygen-concentration output from said oxygen-concentration sensor to thereby control the oxygen concentration of the gas introduced from said first processing chamber to said second processing chamber;

means for accelerating the burning of oxygen and combustible gas components contained in the gas introduced into said second processing chamber; and means for pumping out of said second processing chamber oxygen which remains unconsumed in burning with combustible gas components in said second processing chamber, while maintaining the oxygen concentration in the second processing chamber constant.

8. A gas sensor comprising:

a first processing chamber and a first gas passage for introducing a gas under measurement into said first processing chamber;

a second processing chamber and a second gas passage for introducing the gas from said first processing chamber into said second processing chamber, said second processing chamber burning combustible gas components contained in the gas with oxygen;

a third gas passage for introducing a gas containing oxygen into said processing chamber under diffusion resistance in a predetermined amount in excess of that needed to burn combustible gas components in the second processing chamber;

an oxygen-concentration sensor for sensing the oxygen concentration of the gas introduced from said first processing chamber to said second processing chamber;

a first oxygen pump for pumping oxygen into or pumping oxygen out of the first processing chamber, to thereby control the oxygen concentration of the gas introduced from said first processing chamber to said second processing chamber based on an oxygen-concentration output from said oxygen-concentration sensor;

means for accelerating the burning of oxygen and combustible gas components contained and the gas introduced into said second processing chamber; and means for pumping out of said second processing chamber oxygen which remains unconsumed in burning with combustible gas components in said second processing chamber, while maintaining the oxygen concentration in the second processing chamber constant.

* * * * *